United States Patent [19]
Panagrossi

[11] 3,985,601
[45] Oct. 12, 1976

[54] METHOD FOR PRODUCING A BALLOON TYPE CATHETER HAVING A SMOOTH CONTINUOUS OUTER SURFACE

[75] Inventor: Ahmed Panagrossi, Hamden, Conn.
[73] Assignee: Quantum, Inc., Wallingford, Conn.
[22] Filed: May 5, 1975
[21] Appl. No.: 574,384

[52] U.S. Cl. ............................ 156/229; 128/349 B; 156/244; 156/245; 156/293; 264/291
[51] Int. Cl.² ................ B29C 27/00; B32B 31/30; A61M 25/00
[58] Field of Search ......... 156/244, 245, 293, 294, 156/160, 229; 128/349 R, 349 B, 350 U, 351; 264/291, 292, 293

[56] References Cited
UNITED STATES PATENTS

| | | | |
|---|---|---|---|
| 3,435,826 | 4/1969 | Fogarty | 128/349 B |
| 3,832,253 | 8/1974 | Di Palma et al. | 128/349 B |
| 3,833,003 | 9/1974 | Taricco | 128/349 B |
| 3,833,004 | 9/1974 | Vazquez et al. | 128/349 B |

Primary Examiner—Caleb Weston
Attorney, Agent, or Firm—St. Onge, Mayers, Steward & Reens

[57] ABSTRACT

A method is disclosed for producing an inflatable balloon catheter having an inflatable catheter tip attached to a double lumen catheter shaft to form a smooth, continuous outer surface at the outer juncture of the tip and shaft. The tip is molded and comprises a hollow, thin-walled, cylindrical balloon section that has at least one open end. Mating die members are provided to define a cylindrical mold cavity having inside diameter substantially equal to the inside diameter of the balloon section. The catheter shaft is extruded to have initial outside diameter substantially equal to the outside diameter of the balloon section and, while in a partially cured state, a leading portion of the extruded shaft is stretched to locally reduce its outside diameter. The stretched portion is clamped between the die members in the mold cavity to form a shoulder at a transition between this leading portion and the remainder of the shaft. The entire shaft is then cured. The now permanently reduced diameter shaft portion is stripped from the mold cavity and the balloon section of the catheter tip is installed thereon with the end of the cylindrical balloon section wall adjacent the open end in abutting relation to the shoulder.

9 Claims, 12 Drawing Figures

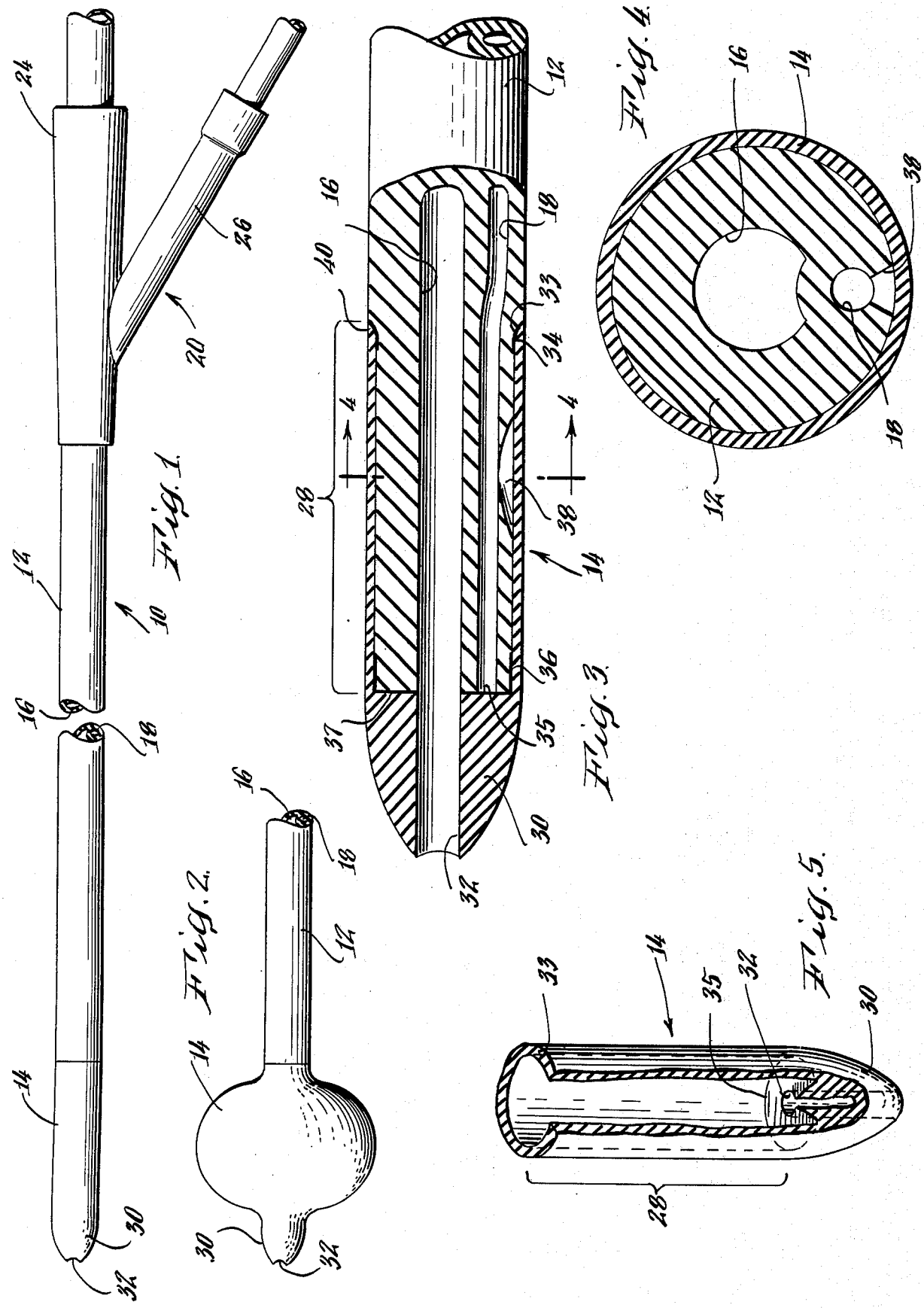

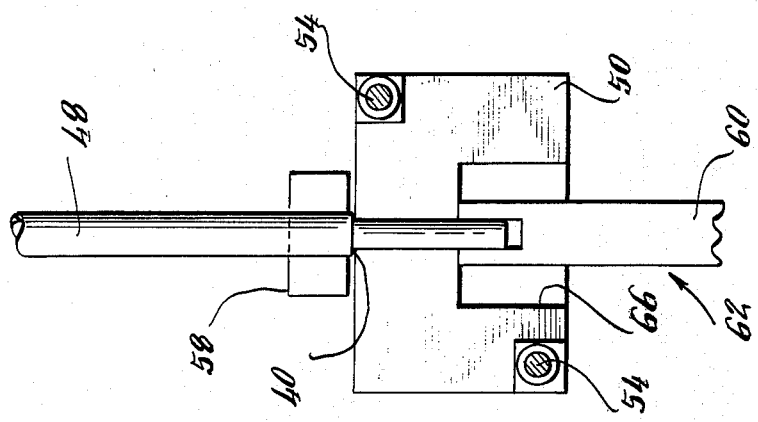
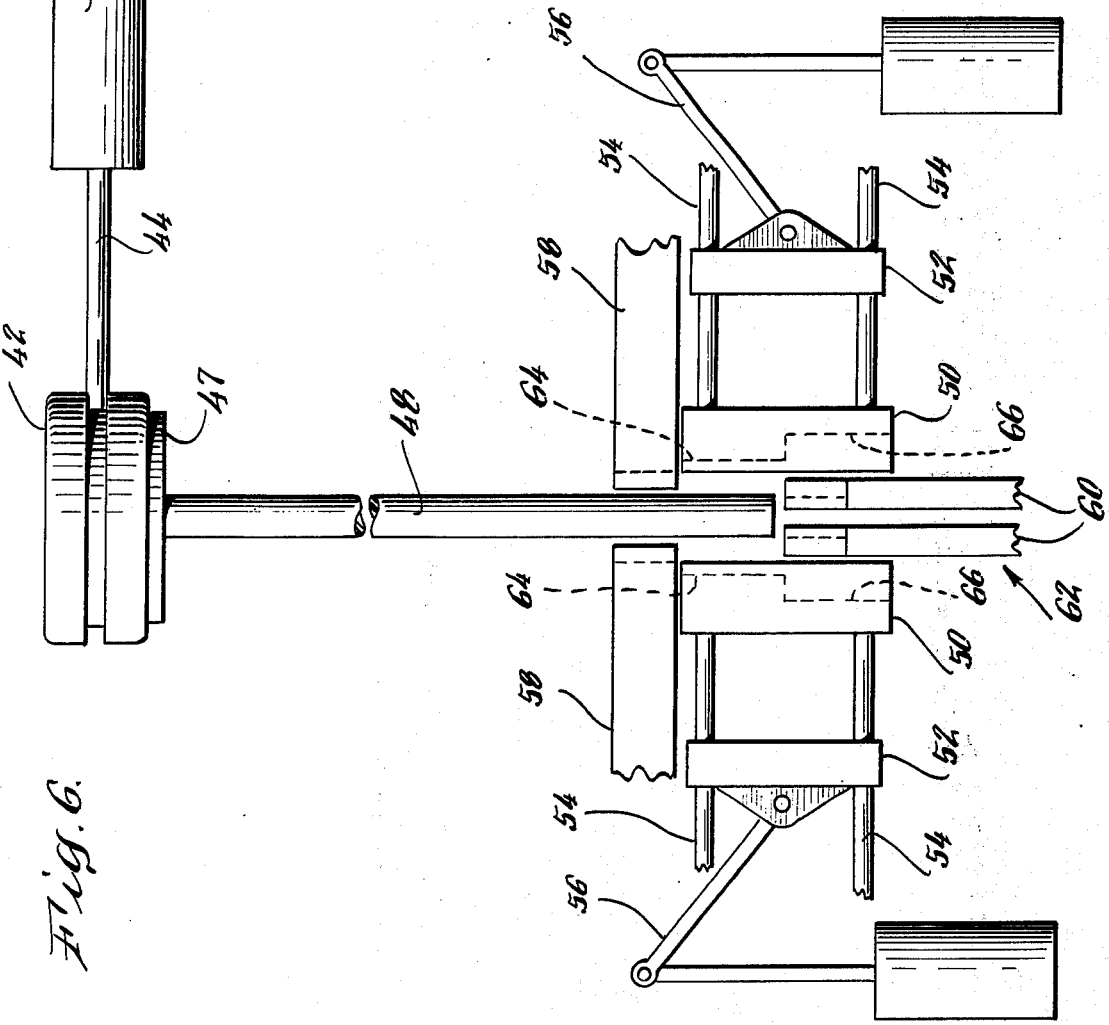

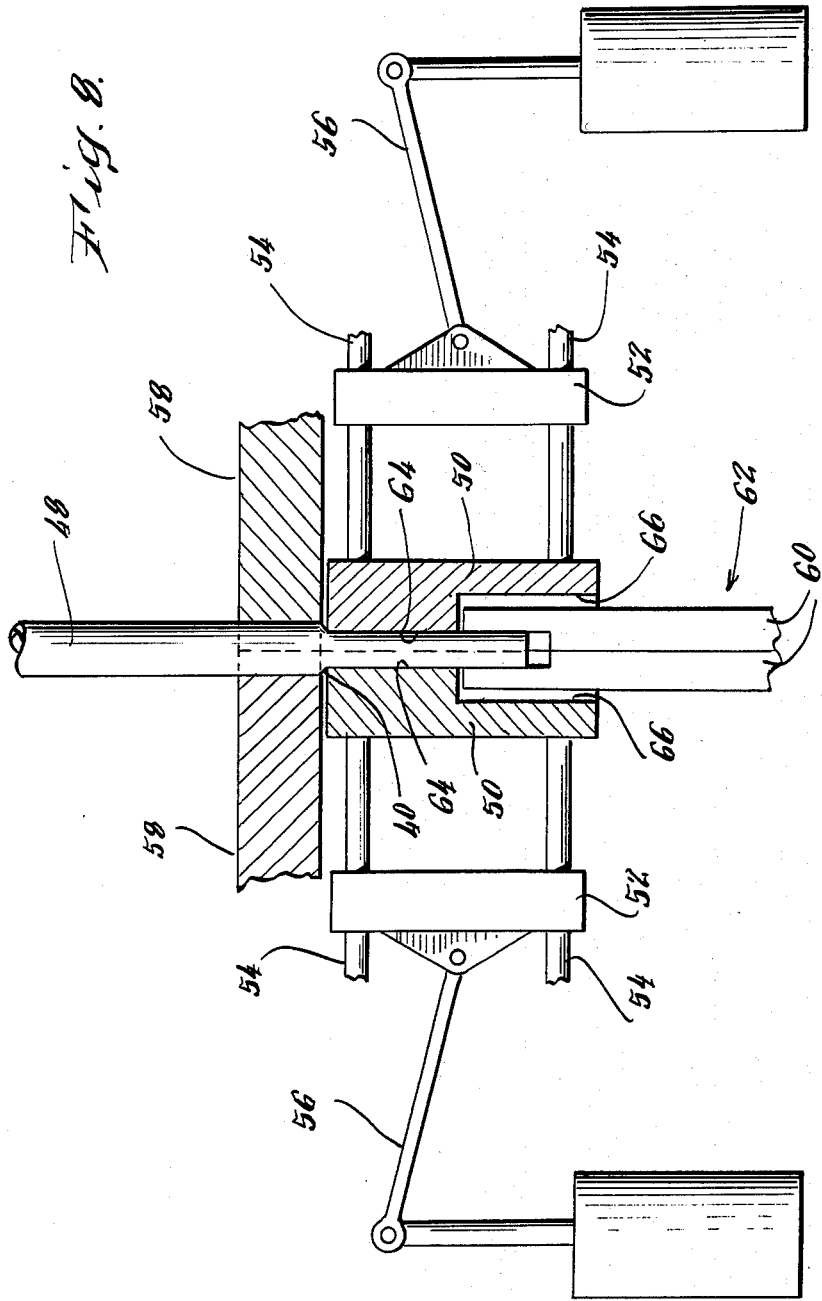
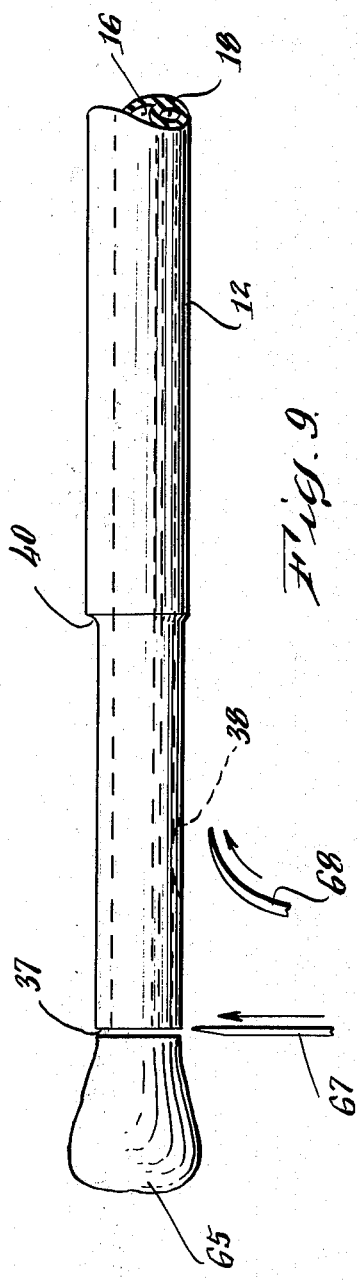

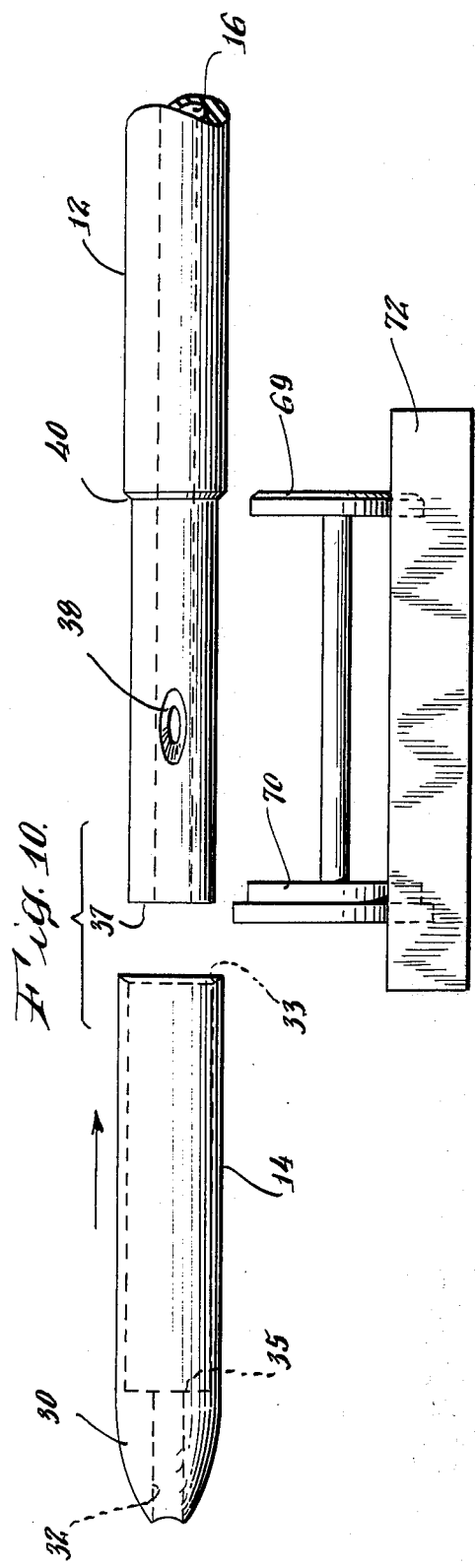
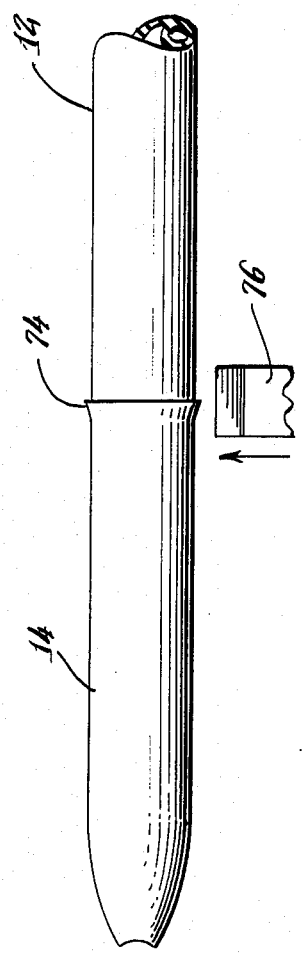
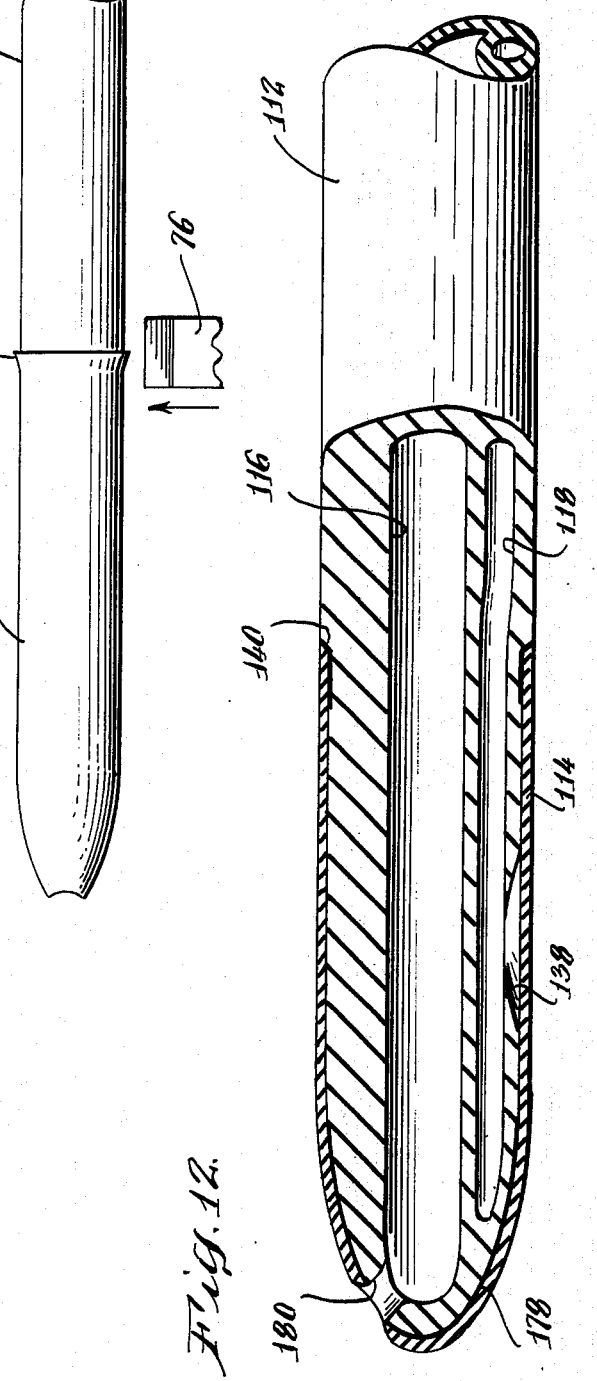

METHOD FOR PRODUCING A BALLOON TYPE CATHETER HAVING A SMOOTH CONTINUOUS OUTER SURFACE

BACKGROUND OF THE INVENTION

1. Field of the Invention

The present invention relates to a method for producing an inflatable balloon catheter which has an inflatable catheter tip and a double lumen catheter shaft joined together in such a manner that a smooth, continuous, outer surface results at their outer juncture.

Inflatable balloon catheters, also known as "Foley catheters," generally are used to drain fluid from or inject fluid into an internal body cavity, for example, the urinary bladder. Such catheters are inserted into the body cavity through an incision or a natural opening, for example, the urethra which leads to the urinary bladder.

Inflatable balloon catheters usually include a flexible, resilient, tubular shaft having two or more passages or lumina extending axially through it. An inflatable balloon is attached at the distal end of the shaft and communicates with one lumen called the inflation lumen. Sterilized, pressurized fluid is pumped through the inflation lumen to inflate the balloon when it is positioned inside the body cavity to be catheterized. The enlarged balloon acts to hold the catheter in position, preventing its disengagement from the cavity.

A second lumen, called the drainage lumen which terminates in one or more drainage eyes, opens into the body cavity so that undesirable fluids can be drained from or medicinal fluids introduced into the cavity.

When it becomes necessary to remove the catheter, the balloon is deflated and the catheter is withdrawn.

To minimize tissue irritation during insertion, operation, and withdrawal of the catheter, both the catheter shaft and balloon tip should be made of an inert, flexible material such as silicone rubber and should be smooth, rounded, and have outside diameter as small as possible yet be large enough to adequately perform the drainage function. That is, the catheter shaft should have sufficiently large diameter to permit the relatively thick-walled construction required to prevent its collapse and to permit the drainage lumen to have inside diameter sufficiently large to minimize chances of occlusion by crystallization of the fluid being drained. The tip should also be rounded so that it may be introduced through the body opening with minimum discomfort. Moreover, the tip should be joined to the catheter shaft to form a smooth, continuous outer junction that itself will not cause irritation, discomfort, or pain. In particular, the balloon tip and shaft should be joined in a way that does not result in a shoulder, rib or, rough trimmed edges at the outer juncture.

DESCRIPTION OF THE PRIOR ART

Inflatable balloon or Foley catheters such as those disclosed in U.S. Pat. Nos. 1,922,084 (Gerow); 2,547,758 (Keeling); 2,642,874 (Keeling); 3,734,100 (Walker et al.); 3,832,253 (Di Palma et al.); and Re. 27,910 (Birtwell) are known. However, some of these catheters, for example, those disclosed in the Di Palma et al. patent, are formed with undesirable circumferential ridges at the locations where the balloon tip is attached to the catheter shaft.

Others, for example, the catheter described in the Gerow patent, are constructed so that the balloon follows the contour of the tube but means by which this construction is made are not disclosed.

Still other catheter constructions attempt to provide a smooth outer surface by attaching an elastic band in an annular undercut or recessed groove in the catheter shaft. The Keeling patents disclose examples of this configuration but do not disclose how the groove is formed. The Walker et al. patent discloses a similar construction in which the tube is incised, presumably cut or ground, to form the groove. The Birtwell patent discloses a design where the balloon tip is attached to a catheter shaft at an undercut seat at the leading shaft end.

However, accurate machining by undercutting or grinding a shaft made of a resilient material such as silicone rubber is difficult and therefore expensive. Machining difficulties are compounded when the shaft and balloon section are not cylindrical, such as these shown in the Walker et al. patent.

SUMMARY OF THE INVENTION

In a preferred embodiment of the present invention, to be described below in detail, the method for producing an inflatable balloon catheter comprises a series of steps for forming the catheter shaft with a lead portion of reduced diameter.

A molded inflatable catheter tip has a thin-walled, hollow, cylindrical balloon section having at least one open end. The balloon section is attached to the reduced diameter shaft portion so that the edge of the cylindrical wall adjacent the open end abuts a shoulder formed on the shaft between the reduced diameter portion and the remainder of the shaft. The outside diameter of the remainder of the catheter shaft and the catheter tip balloon section are chosen to be substantially equal. Therefore, a smooth outer surface is formed at their outer juncture.

This method is practiced by providing mating die members having mold cavity portions which cooperate, when the die members are mated together, to form a cylindrical mold cavity having inside diameter substantially equal to the inside diameter of the catheter tip balloon section. A curable material such as silicone rubber is extruded to form a double lumen catheter shaft having outside diameter substantially equal to the outside diameter of the cylindrical balloon section. While in a partially cured state, a portion of the shaft adjacent its leading end is stretched to sufficiently reduce its outside diameter to permit it to be clamped between the die members in the mold cavity. A shoulder is formed on the shaft's outer surface at the transition between leading reduced diameter portion and the remainder of the shaft in this way. The shaft is then cured and stripped from the mold cavity. The balloon section of the molded catheter tip is installed on the reduced diameter shaft portion with the edge of the cylindrical wall adjacent the open end of the balloon section in abutting relation to the shoulder.

The molded balloon catheter tip may be permanently attached to the catheter shaft by any suitable adhesive or by other means such as heat welding. A port through the shaft wall from the inflation lumen to the space defined between the reduced diameter shaft portion and the balloon section is provided so that balloon may be inflated. A drainage eye is provided between the exterior of the catheter and the drainage lumen to permit drainage.

Catheters produced by the method of the present invention do not require undercutting or grinding of the silicone rubber catheter shaft to provide a reduced diameter shaft portion. Accordingly, expensive and complicated machining steps are eliminated. Rather, the size of the reduced diameter shaft portion is determined more precisely by a mold in which the shaft material is cured. This method is both inexpensive and uncomplicated and results in a smooth, continuous outer catheter surface at the outer juncture of the catheter shaft and catheter tip. Therefore, tissue irritation during insertion, operation, and withdrawal of the catheter are desirably minimized.

Accordingly, it is an object of the present invention to provide a method for producing inflatable balloon catheters having a smooth continuous outer surface in a simple inexpensive way.

Other objects, aspects, and advantages of the present invention will be pointed out, or will be understood from, a consideration of the following detailed description provided below in conjunction with the accompanying drawings.

BRIEF DESCRIPTION OF THE DRAWINGS

FIG. 1 is a side elevational view of an inflatable balloon catheter constructed in accordance with the method of the present invention.

FIG. 2 is a side elevational view of a portion of this catheter shown with the inflatable balloon expanded as it would be after insertion into the body cavity to be drained or supplied with medicinal fluid.

FIG. 3 is an enlarged, vertical, cross-sectional view of the distal end of this catheter shown with the balloon section deflated.

FIG. 4 is a cross-sectional view of the catheter taken through plane 4—4 in FIG. 3.

FIG. 5 is a perspective view, broken away to show detail of the molded inflatable balloon catheter tip.

FIG. 6 is a diagrammatic side elevational view of apparatus for extruding, stretching, and molding the catheter shaft.

FIG. 7 is a diagrammatic front elevational view of one die member shown with the extruded catheter shaft stretched and disposed in the die cavity portion formed on this die member.

FIG. 8 is a diagrammatic cross-sectional view of the molding apparatus shown with the die members mated together and the extruded catheter shaft positioned in the mold cavity.

FIG. 9 is a side elevational view of the catheter shaft showing its molded reduced diameter portion and a diagrammatic view of apparatus for cutting a port from the inflation lumen to the exterior of the shaft.

FIG. 10 is a diagrammatic view of apparatus for applying adhesive to two locations on the catheter shaft for attaching the catheter tip permanently thereto.

FIG. 11 is a side elevational view of the assembled catheter and a diagrammatic view of apparatus for trimming any excess material which might result at the outer juncture of the shaft and tip.

FIG. 12 is a enlarged vertical, cross-sectional view of another balloon catheter construction which may be produced by the method of the present invention.

DESCRIPTION OF THE PREFERRED EMBODIMENTS

FIG. 1 illustrates a typical inflatable balloon catheter, generally indicated at 10, which may be made by the method of the present invention. This catheter 10 includes an extruded catheter shaft 12 and a molded, inflatable balloon catheter tip 14, both of which may or may not be cylindrical. However, in the interest of simplicity the method of the present invention will be described with reference to a cylindrical catheter. Silicone rubber is the material preferred for the shaft and the tip since it is flexible, available in various degrees or softness, and is chemically inert and, hence, nonirritating to body tissue. In particular, certain silicone formulations are well suited for making the inflatable tip since they have excellent durometer, modulus, elongation, and other properties that permit substantial inflation without bursting.

As shown in FIGS. 1 and 2 and in greater detail in FIG. 3, the catheter shaft 12 has a drainage lumen 16 and an inflation lumen 18. A Y-shaped connection 20 is coupled to the proximal end 22 of catheter 10 and has a first leg 24 which communicates with the drainage lumen 16 and a second leg 26 which communicates with the inflation lumen 18. The first leg 24 may be connected to a suitable drainage adaptor for collecting the material which passes through drainage lumen 16 or may be connected to a suitable source of medicinal fluid to be introduced into the body cavity being catheterized. The second leg 26 is connected to a source of selectively pressurized sterile fluid such as distilled water.

As shown in detail in FIGS. 3 and 5, the inflatable catheter tip 14 has a relatively thin-walled, generally cylindrical balloon section 28 integrally formed, for example, by injection molding, with a thick-walled rounded head 30 that defines a cylindrical drainage eye 32. The balloon section terminates at its open end in a circular edge 33 and defines an annular rabbet 35 where it meets the thick-walled head 30. The shaft has a smoothly cut front surface 37 that mates with annular rabbet 35.

The hollow balloon tip section is welded or otherwise secured to the leading portion of the catheter shaft at two locations 34 and 36 to enclose an annular chamber. One or more ports 38 communicate between the inflation lumen 18 and the annular chamber. Accordingly, when sterile fluid is pumped under pressure through inflation lumen 18, the balloon section 28 of catheter tip 14 is inflated into a generally spherical body as shown in FIG. 2.

As shown in detail in FIG. 3, a catheter manufactured by the method of the present invention has a smooth outer surface at the outer juncture of the catheter tip 14 and catheter shaft 12. In particular, the catheter tip has an outside diameter equal to the outside diameter of the main portion of the shaft. The distal end of the shaft has reduced diameter and axial length substantially equal to the inside diameter and axial length, respectively, of the catheter tip balloon section 28. Transition between the reduced diameter portion and remainder of the catheter shaft forms a shoulder 40 and the edge 33 of catheter tip balloon section 28 is installed to abut this shoulder.

The method for producing a catheter such as that described above, may be explained with reference to FIGS. 6 through 11. Referring first to FIGS. 6 through 8, extruding and molding apparatus are diagrammatically illustrated for forming the catheter shaft 16 having a portion at its distal end of reduced diameter. This apparatus includes an extrusion head 42 which is connected by means of a feed tube 44 to a hopper or storage bin 46. Extrusion material is fed from the storage hopper 46 through the feed tube 44 to the extrusion head 42 where it is extruded through a suitable die 47 to form a pliable, uncured, depending tubular parison 48. Parison 48, which has the same inside and outside dimensions as the finished catheter shaft, is received between two die members 50 that are carried on backup plates 52 slidably, reciprocally mounted on a number of rails 54. The die members may be moved between open and closed positions by operation of toggles 56.

Each die member 50 has a die cavity portion 64 which, when die members 50 are in mating relation, define a cylindrical mold cavity having inside diameter substantially equal to the inside diameter of the molded catheter tip balloon section 28.

As shown in FIG. 6, the extruded parison 48 is also received between two opposing clamp members 58 and opposing clamp arms 60 of a drawing tool 62.

When extruded parison 48 reaches the opposing arms 60 of drawing tool 62, both clamp members 58 and the opposing arms 60 are clamped about it. While clamp members 58 hold the upper portion of parison 48 in a vertically, stationary position, drawing tool 62 pulls the portion depending therefrom downward to axially stretch it and thus reduce its diameter. When the parison diameter below clamp members 58 has been sufficiently reduced, the die members are closed about it as shown in FIG. 8.

Mold cavity portions 64 have an enlarged lower sections 66 which accommodate the drawing tool 62 when the die member 50 are closed.

The extruded parison is then cured to form the catheter shaft having the shoulder 40 shown in FIG. 9.

After the curing step has been completed, die members 50 are separated by operating toggles 56, clamp members 58 are opened and cured parison is released from drawing tool 62. The finished catheter shaft is then stripped from the mold cavity.

As shown in FIG. 9, the finished catheter shaft 16 is transported to a station where port 38 is cut in the side wall of the reduced diameter shaft portion by a curved cutting tool 68. The catheter shaft must be properly aligned so that port 38 is located to communicate with the inflation lumen and not the drainage lumen. The reduced diameter portion of the shaft is also trimmed of excess flash 65 to proper axial length by a blade 67 also shown in FIG. 9. Trimming results in the smoothly cut front shaft surface 37.

Referring now to FIG. 10, the catheter shaft 12 and tip 14 are transported to a station where they are assembled. This station may have apparatus which includes two application rollers 69 and 70 for applying a suitable adhesive about the reduced diameter shaft at two portion locations. The first roller is 69 formed to apply adhesive to the shoulder 40. The second roller 70 is formed to apply adhesive to the front surface 37 and side of the leading edge of the reduced diameter catheter shaft portion. The adhesive rollers may also be positioned to pick adhesive up from a reservoir 72.

After the adhesive is applied, the molded catheter tip 14 is installed on the leading reduced diameter catheter shaft portion so that its cylindrical edge 33 abuts the shoulder 40. When so installed, the adhesive secures the tip to the shaft. This assembly results in the annular chamber between the balloon section 28 and the reduced diameter portion of the catheter shaft 12.

The catheter tip may alternatively be circumferentially heat welded to the reduced diameter shaft portion. Heated rollers, spaced the same axial distance as are the adhesive applying rollers, may be employed to bond the tip and shaft together.

After the catheter tip has been attached to the shaft, it may be necessary to trim a small excess portion of material which protrudes away from shoulder 40. As shown in FIG. 11, this excess portion 74 is trimmed by a sharp blade 76 which is either rotated about the catheter or which remains stationary while the catheter rotates by it. Accordingly, when the construction is complete, the catheter has a smooth, continuous outer shaft free from ridges which may cause irritation, discomfort, or pain during catheter insertion, operation, or withdrawal.

FIG. 12 illustrates another construction of an inflatable balloon catheter which may be made by the method of the present invention. This construction includes a catheter shaft 112 having an inflation lumen 118 and a drainage lumen 116. The catheter shaft is also formed with a shoulder 140 by the method described in detail above. That is, after the shaft has been extruded, while in a partially cured state, the distal end is stretched and clamped between opposing die members. There it is cured to form the reduced diameter portion and shoulder. However, the drawing tool 62 described above, is designed to close off the end of the extruded catheter shaft to seal inflation and drainage lumina 118 and 116.

In this construction, catheter tip 114 is not formed with a thick-walled head as shown in FIG. 3 at 30. Rather, the catheter tip 114 is in the form of a simple sleeve having one closed end and uniform wall thickness throughout.

The reduced diameter catheter shaft portion is formed with diameter substantially equal to the inside diameter of the catheter tip. Similarly, the outside diameter of the remainder of the shaft and the tip are substantially equal. Port 138 is cut in the side wall of the reduced diameter shaft portion to communicate with inflation lumen 118. The tip is then installed on the shaft to complete a smooth, continuous outer surface at their juncture. A drainage eye 180 is cut through both the catheter tip and shaft to communicate with the drainage lumen 116 at a point not between the two points at which the tip is attached to the shaft.

As noted, the method of the present invention may be used to produce catheters which do not have cylindrical cross-sections. In such cases, the molded catheter tip has a tubular balloon section which define non-circular inside and outside tubular shapes such as, for example, elliptical shapes. This method is then practiced by providing mating die members which have mold cavity portions that cooperate to form a tubular mold cavity having the same tubular shape and size as the tip's balloon section inside tubular shape. The catheter shaft is extruded to have the same tubular shape and size as the balloon section outside tubular shape. A portion of the shaft is stretched while in a partially curved state to reduce this portion's tubular size. The smaller portion is then clamped in the mold cavity. Other steps of the method are practiced as described above.

Although a preferred embodiment of the present invention has been described above in detail, it is to be understood that this is only for purposes of illustration. Modifications may be made to the described method for producing an inflationable balloon type catheter having a smooth, continuous outer surface at the juncture between the catheter shaft and tip by those skilled in the art in order to adapt this method to particular applications.

What is claimed is:

1. A method of producing an inflatable balloon catheter having an inflatable balloon catheter tip attached to a multiple lumen catheter shaft to form a smooth, continuous outer surface at the outer juncture of said tip and shaft, said tip comprising a hollow tubular balloon section defining inside and outside tubular shapes, said method comprising the steps of:

providing mating die members having mold cavity portions which cooperate when said die members are mated together to form a tubular mold cavity having the same tubular shape and size as the balloon section inside tubular shape;

extruding a curable material to form said catheter shaft having the same tubular shape and size as the balloon section outside tubular shape;

axially stretching a portion of said shaft adjacent its leading end while in a partially cured state to reduce the tubular size of said portion;

clamping said shaft portion between said die members in said mold cavity to form said shaft portion with the same tubular shape and size as the balloon section inside tubular shape and to form a shoulder at each juncture of said portion and the remainder of said shaft;

curing said shaft;

stripping said shaft portion from said mold cavity; and installing said balloon section on said shaft portion.

2. A method of producing an inflatable balloon catheter having an inflatable balloon catheter tip attached to a multiple lumen catheter shaft to form a smooth, continuous outer surface at the juncture of said tip and shaft, said tip including a hollow, cylindrical balloon section, having at least one open end and at least one circular edge about the open end, said method comprising the steps of:

providing mating die members having mold cavity portions which cooperate when said die members are mated together to form a cylindrical mold cavity having inside diameter substantially equal to the inside diameter of said balloon section;

extruding a curable material to form said catheter shaft having outside diameter substantially equal to the outside diameter of said balloon section;

axially stretching a portion of said shaft adjacent its leading end while in a partially cured state to reduce the outside diameter of said portion;

clamping said shaft portion between said die members in said mold cavity to form a shoulder at the juncture of said shaft portion and the remainder of said shaft;

curing said shaft;

stripping said portion from said mold cavity; and shaft portion with the circular edge in abutting relation to said shoulder.

3. The method for producing an inflatable balloon catheter as claimed in claim 2 further comprising the step of:

trimming excess balloon section material from about said shoulder after said installing step.

4. The method for producing an inflatable balloon catheter as claimed in claim 2 wherein said shaft has an inflation lumen and said method further comprises the step of:

providing fluid communication between said inflation lumen and the space defined between said balloon section of said catheter tip and said reduced diameter shaft portion.

5. The method for producing an inflatable balloon catheter as claimed in claim 2 wherein said shaft has an inflation lumen and a drainage lumen and said method further comprises the steps of:

circumferentially binding said catheter tip balloon section to said reduced diameter shaft portion at at least two locations;

providing fluid communication from said inflation lumen to the space between said balloon section and said reduced diameter shaft portion at a point between said circumferential binding locations; and providing fluid communication from said drainage lumen to the exterior of said catheter at a point not between said circumferential binding location.

6. The method for producing an inflatable balloon catheter as claimed in claim 2 further comprising the step of:

circumferentially binding said balloon section of said catheter tip to said reduced diameter shaft portion in at least one axial location.

7. The method for producing an inflatable balloon catheter as claimed in claim 6 wherein at least one of said axial locations is at said reduced diameter shaft portion adjacent said shoulder.

8. The method for producing an inflatable balloon catheter as claimed in claim 6 wherein said binding step comprises the step of:

applying adhesive at said binding locations prior to said installation step.

9. The method for producing an inflatable balloon catheter as claimed in claim 6 wherein said binding step comprises the step of:

heat welding said tip to said shaft at said binding locations after said installation step.

* * * * *